(12) United States Patent
Hirano

(10) Patent No.: US 8,786,865 B2
(45) Date of Patent: Jul. 22, 2014

(54) ASPERITY DETECTION DEVICE FOR CAN

(75) Inventor: Tadafumi Hirano, Sunto-gun (JP)

(73) Assignee: Universal Can Corporation, Tokyo (JP)

( * ) Notice: Subject to any disclaimer, the term of this patent is extended or adjusted under 35 U.S.C. 154(b) by 0 days.

(21) Appl. No.: 13/513,646

(22) PCT Filed: Dec. 16, 2010

(86) PCT No.: PCT/JP2010/072688
§ 371 (c)(1), (2), (4) Date: Jun. 4, 2012

(87) PCT Pub. No.: WO2011/078057
PCT Pub. Date: Jun. 30, 2011

(65) Prior Publication Data
US 2012/0243003 A1  Sep. 27, 2012

(30) Foreign Application Priority Data

Dec. 22, 2009 (JP) ................. 2009-291183

(51) Int. Cl.
| | |
|---|---|
| *G01B 11/30* | (2006.01) |
| *G01N 21/55* | (2014.01) |
| *G01N 21/00* | (2006.01) |
| *G06K 9/00* | (2006.01) |
| *H04N 9/47* | (2006.01) |
| *H04N 7/18* | (2006.01) |
| *B07C 5/12* | (2006.01) |
| *B07C 5/34* | (2006.01) |
| *G01N 21/90* | (2006.01) |
| *B07C 5/00* | (2006.01) |

(52) U.S. Cl.
USPC ........ 356/600; 356/445; 356/240.1; 382/141; 348/86; 348/128; 348/131; 250/223 B; 209/587

(58) Field of Classification Search
None
See application file for complete search history.

(56) References Cited

U.S. PATENT DOCUMENTS 2,219,572 A * 10/1940 Everett ................... 356/239.4
4,284,353 A *  8/1981 Yoshida et al. ......... 356/239.4
(Continued)

FOREIGN PATENT DOCUMENTS

| EP | 0952443 A1 | 10/1999 |
|---|---|---|
| JP | 2003-215055 A | 7/2003 |

(Continued)

OTHER PUBLICATIONS

International Search Report dated Jan. 25, 2011, issue for PCT/JP2010/072688.

*Primary Examiner* — Gordon J Stock, Jr.
(74) *Attorney, Agent, or Firm* — Edwards Wildman Palmer LLP

(57) ABSTRACT

Provided is an asperity detection device for a can which does not need an additional conveyance device for inspection, reduces increased inspection costs, and allows for quick detection of defective merchandise while conveying the can. The asperity detection device for a can is provided with: first lighting devices (30) which irradiate a first light substantially horizontal to a top surface (21a) of a mouth section (21) from a side of a can (20); a second lighting device (40) which irradiates a second light substantially vertical to the top surface (21a) of the mouth section (21) from above the can (20); and an imaging device (50) which is arranged above the can (20), photographs the top surface (21a) of the mouth section (21), and detects reflection at the top surface (21a), in which at least three or more first lighting devices (30) are arranged with substantially even intervals in a circumferential direction around a periphery of the mouth section (21), the first light which is irradiated from each of the first lighting devices (30) is irradiated to the top surface (21a) from a side of the mouth section (21) along a tangent line of a cylindrical surface of the mouth section (21) substantially horizontal so that an optical axis is not coincide with the optical axes of the other first lights.

2 Claims, 4 Drawing Sheets

(56) References Cited

U.S. PATENT DOCUMENTS

| | | | | |
|---|---|---|---|---|
| 4,391,373 | A | * | 7/1983 | Wiggins ................ 209/526 |
| 4,650,326 | A | * | 3/1987 | Nagamine et al. ......... 356/239.4 |
| 4,697,076 | A | * | 9/1987 | Yoshida ................ 250/223 B |
| 4,758,084 | A | * | 7/1988 | Tokumi et al. ............ 356/239.4 |
| 4,972,093 | A | * | 11/1990 | Cochran et al. .......... 250/559.08 |
| 5,020,908 | A | * | 6/1991 | Hermann ................ 356/239.1 |
| 5,072,107 | A | * | 12/1991 | Apter ................ 250/223 B |
| 5,134,278 | A | * | 7/1992 | Nelen ................ 250/223 B |
| 6,072,575 | A | * | 6/2000 | Loll ................ 356/239.4 |
| 6,122,048 | A | * | 9/2000 | Cochran et al. ............ 356/239.4 |
| 6,275,287 | B1 | * | 8/2001 | Watanabe ................ 356/239.4 |
| 6,621,569 | B2 | * | 9/2003 | Sones ................ 356/237.2 |
| 7,488,965 | B2 | * | 2/2009 | Cochran et al. .......... 250/559.45 |
| 8,014,586 | B2 | * | 9/2011 | Sones et al. .................... 382/149 |
| 2003/0113491 | A1 | * | 6/2003 | Beck et al. .................. 428/35.7 |

FOREIGN PATENT DOCUMENTS

| | | |
|---|---|---|
| JP | 2003-302350 A | 10/2003 |
| JP | 2004-083128 A | 3/2004 |
| JP | 2004-264132 A | 9/2004 |
| JP | 2007-084081 A | 4/2007 |
| WO | WO 2012169471 A1 * | 12/2012 |

* cited by examiner

ASPERITY DETECTION DEVICE FOR CAN

The present invention relates to an asperity detection device for a can.

Priority is claimed on Japanese Patent Application No. 2009-291183, filed Dec. 22, 2009, the content of which is incorporated herein by reference.

BACKGROUND OF THE INVENTION

1. Field of the Invention

A can having a bottle-shape of aluminum alloy in which a cap is screwed on a mouth section having a screw is known as a container filled with contents such as drinks. The can is manufactured by: forming an aluminum alloy sheet into a closed-end cylindrical body which has a bottom plate and a cylindrical side surface in one piece by performing drawing processing and ironing processing (i.e., DI forming); coating an inner surface and an outer surface of the close-ended cylindrical body; forming a shoulder and the mouth section by performing so-called neck-in processing on an aperture section; and performing screw-forming processing, curl-forming processing and the like on the mouth section.

2. Description of Related Art

An inner coating in the can is formed by thermo-setting resin such as epoxy-acrylic resin, polyester resin or the like in order to make corrosion resistance and so on to the can with respect to content of the can (refer to Patent Document 1). The inner coating is formed by spraying paint on an inner surface of the can after the drawing and ironing processing before the neck-in processing. However, the paint may scatter around or may cleave to the outer surface of the can and tiny protrusions are formed, so that the protrusions may preface with corrugations when the neck-in processing is performed.

A curl portion is formed by folding an upper end of the mouth section outward and the inner coating is formed an outer surface of the curl portion. The can is hermetically sealed by attaching a cap so as to press a liner to the curl portion (refer to Patent Document 2). Therefore, if asperity such as the aforementioned corrugations by the paint is formed on the surface of the curl portion, especially on a top surface, the content may be leaked.

Therefore, it is important that the asperity such as the corrugations and the like are not formed on the top surface of the curl portion. Furthermore, in case of the asperity is formed, it is expected that the asperity is detected in an inspection process and reliably excluded as a defective.

In addition, there is a case in which asperity is formed on the surface of the curl portion by the inner coating being crumpled when the mouth section or the curl portion is formed.

For example, as a detection method for detecting fine asperity (e.g., corrugation or the like) formed on the outer surface, a detection method in which a can-body is irradiated obliquely to a tangent plane (i.e., a plane along a tangent line of the outer surface) so that corrugations are detected by observing reflection or shade of the corrugations along the tangent plane is suggested (refer to Patent Document 3).

PRIOR ART DOCUMENT

Patent Document

Patent Document 1: Japanese Unexamined Patent Application, First Publication No. 2007-84081
Patent Document 2: Japanese Unexamined Patent Application, First Publication No. 2004-83128
Patent Document 3: Japanese Unexamined Patent Application, First Publication No. 2004-264132

SUMMARY OF THE INVENTION

Problems to be Solved by the Invention

However, since the detection method described in Patent Document 3 is a detection method of a surface of a can-body, a can as an object should be rotated, and it is not possible to inspect at a single-row conveyer provided at a traditional manufacturing line. Therefore, since an additional conveyance device rotating the can during the inspection should be provided, cost is increased and manufacturing speed is deteriorated.

Means for Solving the Problem

The present invention is contrived in view of the circumstances and an object of the present invention is to provide an asperity detection device for a can in which an additional conveyance device for inspection is not necessary, which reduces increased inspection costs, and allows for quick detection of defective merchandise without stopping the conveyance.

The present invention is an asperity detection device for a can which detects asperity of a can at a top surface of a mouth section during single-row conveyance, the can having the mouth section in which a curl portion is formed by curling an aperture end of the mouth section outward so that a cap with liner is attached to the mouth section, including: first lighting devices which irradiate a first light substantially horizontal to the top surface of the mouth section from a side of the can; a second lighting device which irradiates a second light substantially vertical to the top surface of the mouth section from above the can; and an imaging device which is arranged above the can, photographs the top surface of the mouth section, and detects reflection at the top surface. In the asperity detection device, at least three or more first lighting devices are arranged with substantially even intervals with each other in a circumferential direction around a periphery of the mouth section, the first light which is irradiated from each of the first lighting devices is irradiated to the top surface from a side of the mouth section along a tangent line of a cylindrical surface of the mouth section substantially horizontal so that an optical axis is not coincide with the optical axes of the other first lights.

According to the detection device, since the lights are irradiated at the top surface by the first lighting devices from three or more direction so that the optical axes are along the surface direction, diffusion or shade are formed at the asperity. Furthermore, by flatly lighting the whole top surface by the second lighting device, color-figure which does not have asperity such as roll-figure of the aluminum material, punch-figure by the DI forming or blots can be prevented from being detected as the asperity. As a result, the asperity of the mouth section which deteriorates sealing performance can be quickly and reliably detected without stopping the single-row conveyance.

In order to detect the asperity at the top surface, it is conceivable to photograph an image of the top surface of the mouth section from the side of the can. In this case, in order to inspect the whole top surface of the mouth section, it is necessary to photograph more than once while rotating the can. However, a device for rotating the can is not provided usually with the conveyance device of a manufacturing line, so that increase in cost due to an addition of the rotating device may be a problem. Also, it may take a long for the inspection since the can is rotated, so that manufacturing speed may be deteriorated.

In the detection device according to the present invention, the top surface of the mouth section is irradiated by the lights from multiple direction around the mouth section and from the above the mouth section. Therefore, it is necessary only to photograph the whole top surface from the above in order to obtain an image in which the asperity can be detected, so that the inspection can be operated quickly at low cost without stopping the conveyance.

Furthermore, in this detection device, it is preferable that the first light and the second light be monochromatic lights and be complementary with each other. In this case, in a state in which the top surface is evenly irradiated by the second light, shade or diffusion by the asperity are generated by complementarily lighting of the first light from the side. The reflection in which the first light and the second light are mixed is separated, so that the asperity can be clearly detected by the reflection of the first light. Also, roll-figure of the aluminum material, punch-figure of DI forming, a blot and the like are prevented from being detected.

Effects of the Invention

According to the can asperity detection device of the present invention, the addition of the conveyance device for inspection and the like is not necessary, the inspection cost is reduced, and the defective merchandise having the asperity at the top surface of the mouth section can be quickly detected without stopping the single-row conveyance.

DESCRIPTION OF THE PREFERRED EMBODIMENTS

Hereinafter, an embodiment of an asperity detection device for a can according to the present invention will be described.

A can 20 which is inspected in an asperity detection device 10 has a mouth section 21 (for example, diameter thereof is 38 mm) in which a screw is formed on a cylindrical part thereof, and is conveyed by a conveyer 11 at single-row in a manufacturing line. The asperity detection device 10 is provided at a middle of the single-row conveyance path in the manufacturing line of the can 20. In the asperity detection device 10, without stopping or rotating the can 20, asperity of the mouth section 21 can be detected during the single-row conveyance.

Figure 1:
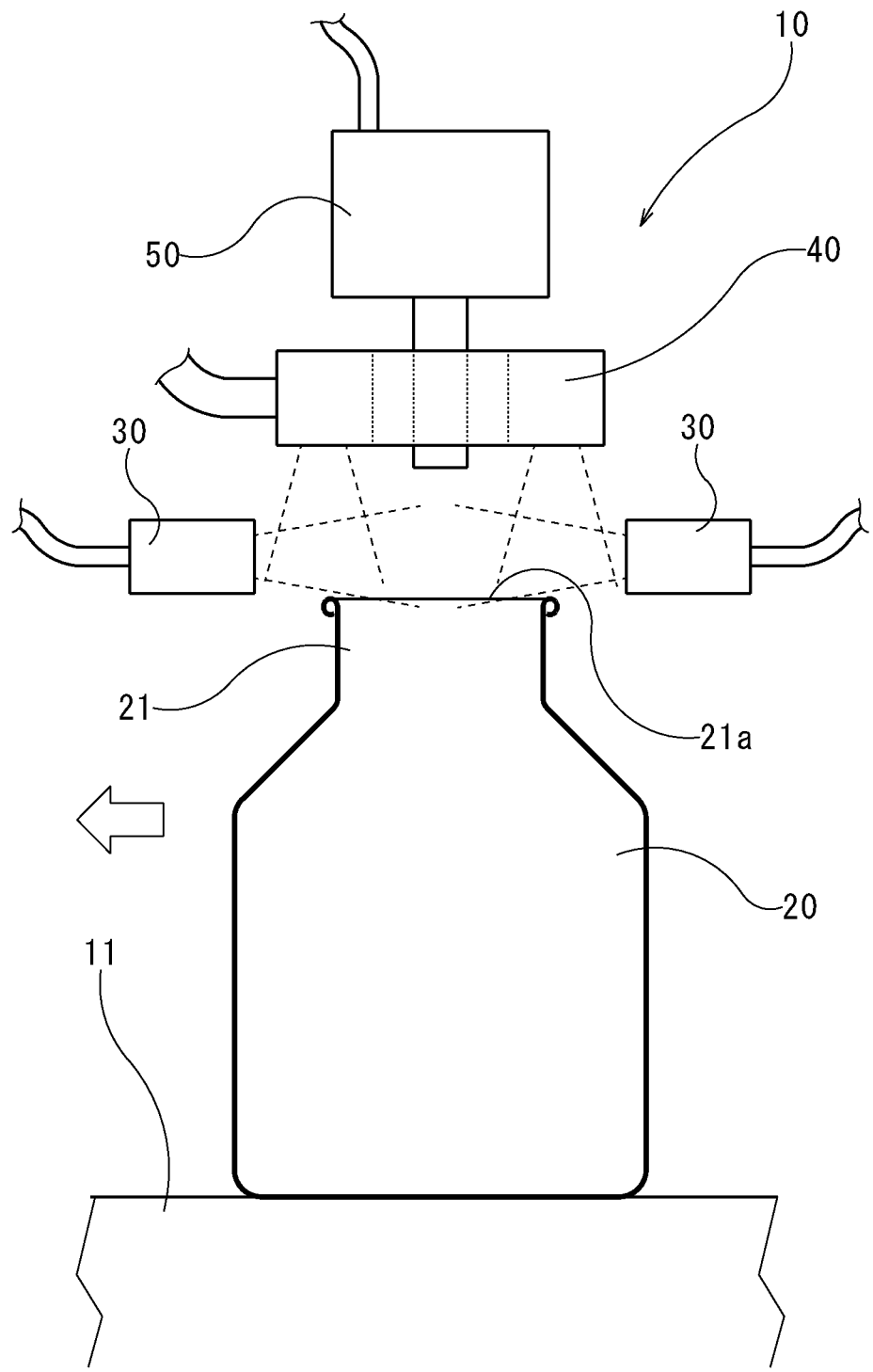
FIG. 1 is a side view showing an asperity detection device for a can of the present invention.

As shown in FIG. 1, the asperity detection device 10 is provided with: a plurality of first lighting devices 30 which irradiate a first light substantially horizontal to a top surface 21a of the mouth section 21 from a side of the can 20; a second lighting device 40 which irradiates a second light substantially vertical to the top surface 21a of the mouth section 21 from above the can 20; and an imaging device 50 which is arranged above the can 20 and photographs the top surface 21a of the mouth section 21.

Figure 2:
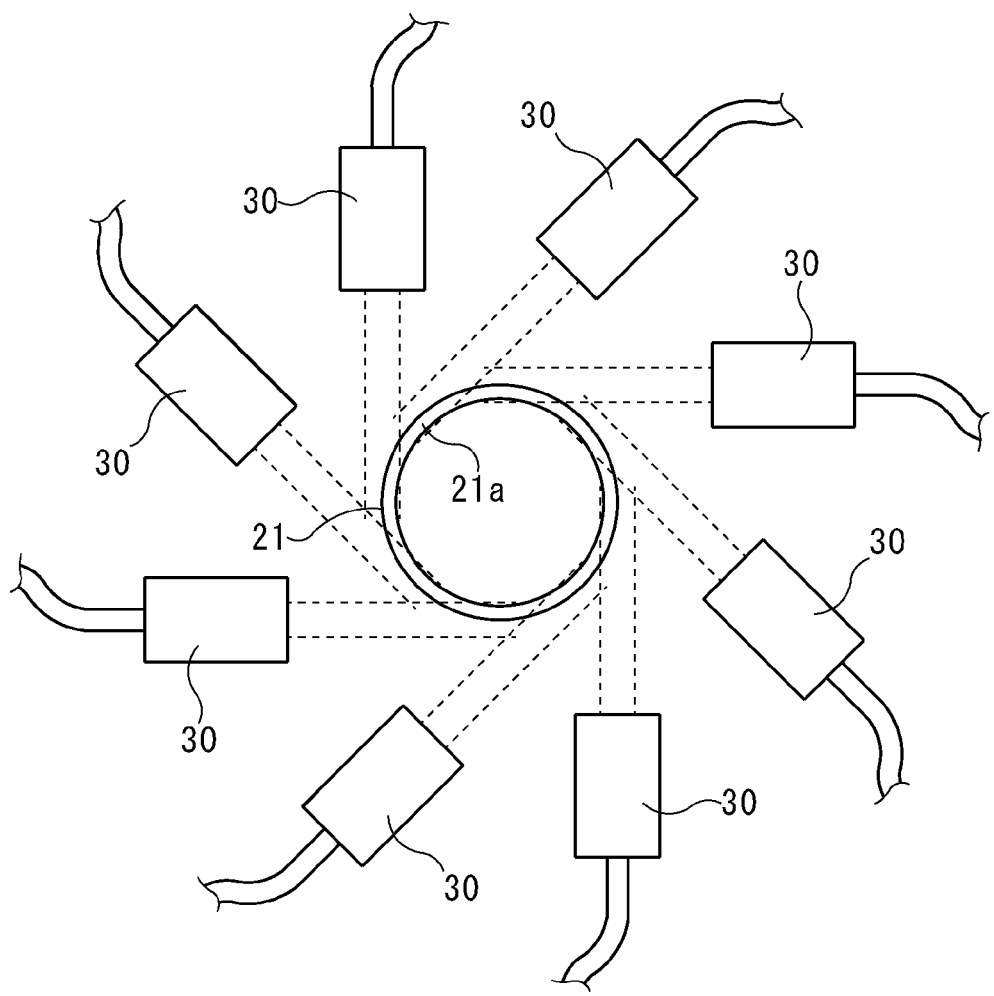
FIG. 2 is a top view showing the asperity detection device of FIG. 1 and a can.

Each of the first lighting device 30 is a light source which can evenly irradiate a linear light having width of 8 mm and height of 1 mm from a plurality of optical fibers. As shown in FIG. 2, the three or more (eight in the present embodiment) first lighting devices 30 are arranged with substantially even intervals in a circumferential direction around a periphery of the mouth section 21. A number of the first lighting device 30 is appropriately selected so as to illuminate a whole surface of the mouth section 21 in accordance with the width and irradiation angle of the irradiated light by the first lighting device 30.

Each of the first lighting devices 30 irradiates the first light from a side of the mouth section 21 to the top surface 21a along a tangent line of a cylindrical surface of the mouth section 21 substantially horizontal so that an optical axis is not coincide with the optical axes of the other first lights, as shown in FIG. 2. The first light is, for example, monochromatic light such as red or the like.

The second lighting device 40 is a light source which can irradiate an even circular light from a plurality of optical fibers, arranged concentrically with the mouth section 21 of the can 20, and irradiates the monochromatic second light evenly to the top surface 21a of the mouth section 21 from above substantially vertical. The second light is complementary color light with the first light. For example, in a case in which the light color of the first light is red, the light color of the second light is blue, so that a reflection at a lap of the first light and the second light (i.e., a part of asperity which is formed on the top surface 21a) is purple. Two colors of lights which are complementary with each other are used since the two colors can be easily separated even though those are mixed.

The imaging device 50 is a so-called area sensor camera, photographs the whole top surface 21a of the mouth section 21 through an inner of the second lighting device 40 from above the can 20, and detects reflection of the first light and the second light at the top surface 21a. The image is binarized so as to define the asperity by distilling the first light.

The inspection of the can 20 using the asperity detection device 10 constructed as above will be described.

As shown in FIG. 1, the can 20 passes the asperity detection device 10 as conveyed by the conveyer 11. At this time, the asperity detection device 10 illuminates the top surface 21a of the mouth section 21 of the can 20 by the first lighting device 30 and the second lighting device 40, and photographs the top surface 21a by the imaging device 50.

Figure 3:
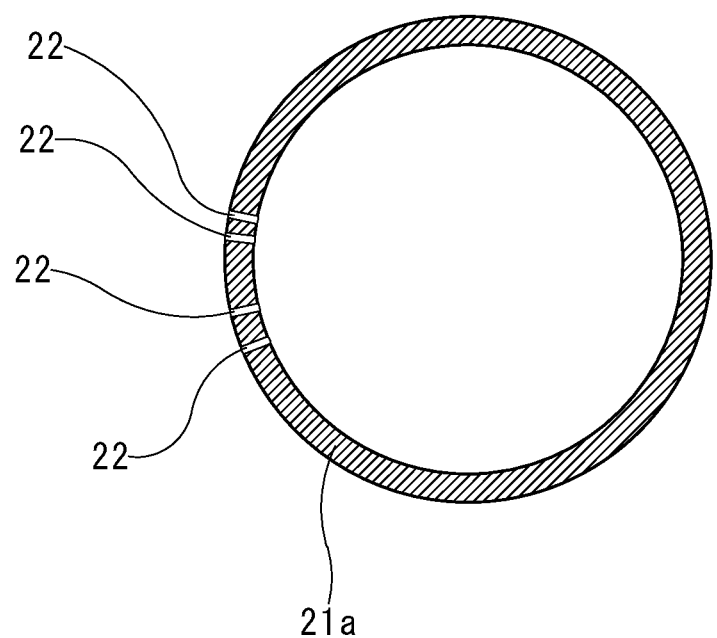
FIG. 3 is a top view showing a top surface of the can in which protrusions are formed.

The shot image is, as shown in FIG. 3, binarized so that the asperity on the top surface 21a is defined by distilling the first light. If protrusions 22 are formed on the top surface 21a, for example, as an inner coating 23 is crumpled by the drawing and ironing processing, the image of the protrusions 22 can be obtained. Therefore, by scanning the image along the circumferential direction of the mouth section 21, the protrusions 22 can be detected.

In order to obtain an image in which the protrusions 22 can be clearly detected, the asperity detection device 10 is provided with the first lighting device 30 and the second lighting device 40, and illuminates the top surface 21a from two directions. If the top surface 21a is illuminated only from the above or only from the side, there is a case in which the protrusions 22 may not be clear, and not only the reflection and shade by the protrusions 22, but differences of color having no asperity such as the roll-figure of an aluminum material 24, the punch-figure by DI forming, blots and the like may be detected.

Figure 4:
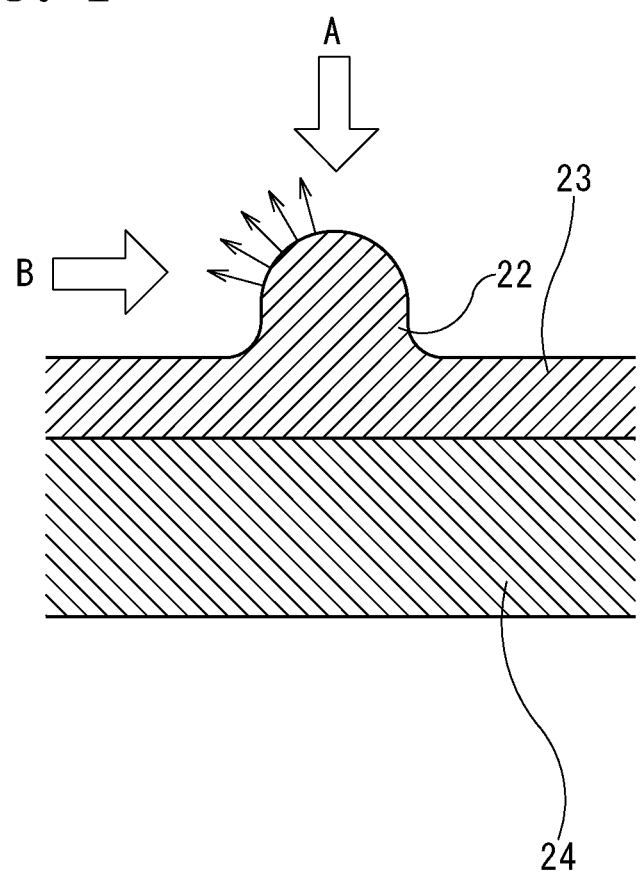
FIG. 4 is a sectional view showing the protrusion which is formed on the top surface of the can.

In the asperity detection device 10, as shown by an arrow A in FIG. 4, by irradiating the monochromatic second light to the whole top surface 21a along a photographing direction, the color of the roll-figure, the punch-figure, the blots and the like of the aluminum material 24 are degraded. Furthermore, as shown by an arrow B, since the first light is irradiated from the side by the first lighting device 30, the first light is reflected at the protrusions 22. Since the first light and the second light are complementary with each other, a process to distill one of the colors is easy, so that a sharp image of the protrusions 22 can be clearly detected as shown in FIG. 3.

As described above, according to the asperity detection device 10, since the asperity is confirmed by photographing the whole top surface 21a of the mouth section 21, the can 20 is not necessary to be rotated, so that the increase of the inspection cost can be reduced and the defective merchandise can be detected in the short inspection time without deteriorating the manufacturing speed. Also, by using the lights from two directions, only the asperity can be clearly detected, so that the roll-figure of the aluminum material, the punch-figure by DI forming, the blots and the like can be prevented from being detected as a defective.

The present invention is not limited to the above-described embodiments and various modifications in details may be made without departing from the scope of the present invention.

INDUSTRIAL APPLICABILITY

Since the lights are irradiated at the top surface by the first lighting devices so that the optical axes are along the surface direction, diffusion or shade are formed at the asperity. Furthermore, by flatly lighting the whole top surface by the second lighting device, color-figure without asperity such as roll-figure of the aluminum material, punch-figure by DI forming, blots and the like are prevented from being detected as the asperity. As a result, the asperity of the mouth section which deteriorates sealing performance can be quickly and reliably detected without stopping the single-row conveyance.

REFERENCE SYMBOLS 10 asperity detection device
11 conveyer
20 can
21 mouth section
21a top surface
22 protrusion
23 inner coating
24 aluminum material
30 first lighting device
40 second lighting device
50 imaging device

What is claimed is:

1. An asperity detection device for an aluminum can which detects asperity of the aluminum can at a top surface of a mouth section during single-row conveyance, the can having the mouth section in which a curl portion is formed by curling an aperture end of the mouth section outward so that a cap with liner is attached to the mouth section, comprising:

first lighting devices which irradiate a first light horizontal to the top surface of the mouth section from a side of the aluminum can;

a second lighting device which irradiates a second light vertical to the top surface of the mouth section from above the aluminum can; and an imaging device which is arranged above the aluminum can, photographs the top surface of the mouth section, and detects reflection at the top surface, wherein three or more first lighting devices are arranged with even intervals in a circumferential direction around a periphery of the mouth section so as to irradiate the first light to the top surface from a side of the mouth section along tangent lines of a cylindrical surface of the mouth section horizontal so that each of optical axes of the first light does not coincide with another optical axes of the first light and each of irradiation positions of the first light is shifted from another irradiation positions of the first light.

2. The asperity detection device for an aluminum can according to claim 1, wherein the first light and the second light are monochromatic lights and are complementary with each other.

* * * * *